(12) United States Patent
Timlin et al.

(10) Patent No.: US 8,686,363 B1
(45) Date of Patent: Apr. 1, 2014

(54) HYPERSPECTRAL STIMULATED EMISSION DEPLETION MICROSCOPY AND METHODS OF USE THEREOF

(75) Inventors: Jerilyn A. Timlin, Albuquerque, NM (US); Jesse S. Aaron, Salt Lake City, UT (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 13/609,057

(22) Filed: Sep. 10, 2012

(51) Int. Cl.
*G01J 5/02* (2006.01)

(52) U.S. Cl.
USPC .................................................. 250/339.07

(58) Field of Classification Search
USPC ....................................... 250/339.01–339.15
See application file for complete search history.

(56) References Cited

U.S. PATENT DOCUMENTS

| | | | |
|---|---|---|---|
| 6,341,257 B1 | 1/2002 | Haaland | |
| 6,415,233 B1 | 7/2002 | Haaland | |
| 6,584,413 B1 | 6/2003 | Keenan et al. | |
| 6,675,106 B1 | 1/2004 | Keenan et al. | |
| 6,687,620 B1 | 2/2004 | Haaland et al. | |
| 6,711,503 B2 | 3/2004 | Haaland | |
| 6,721,094 B1 | 4/2004 | Sinclair et al. | |
| 6,842,702 B2 | 1/2005 | Halland et al. | |
| 6,922,645 B2 | 7/2005 | Halland et al. | |
| 6,967,757 B1 | 11/2005 | Allen et al. | |
| 7,034,271 B1 | 4/2006 | Sinclair et al. | |
| 7,283,684 B1 | 10/2007 | Keenan | |
| 7,400,772 B1 | 7/2008 | Keenan | |
| 7,449,699 B1 | 11/2008 | Adams et al. | |
| 7,451,173 B1 | 11/2008 | Van Benthem et al. | |
| 7,472,153 B1 | 12/2008 | Keenan | |
| 7,491,944 B1 | 2/2009 | Stork et al. | |
| 7,683,310 B1 | 3/2010 | Sinclar et al. | |
| 7,697,134 B1 | 4/2010 | Sinclar et al. | |
| 7,725,517 B1 | 5/2010 | Keenan | |
| 8,441,633 B2 * | 5/2013 | Truong et al. | 356/301 |
| 2005/0043902 A1 * | 2/2005 | Haaland et al. | 702/30 |
| 2012/0292531 A1 * | 11/2012 | Grudinin et al. | 250/459.1 |

OTHER PUBLICATIONS

Wildanger et al., "STED microscopy with a supercontinuum laser source," 2008, Optics Expres, vol. 16, No. 13, pp. 9614-9621.*
H. Sahoo, "Forster resonance energy transfer—A spectroscopic nanoruler: Principle and applications," 2011, Journal of Photochemistry and Photobiology C: Photochemistry Reviews 12, pp. 20-30.*
U.S. Appl. No. 11/334,840, filed Jan. 19, 2006, Timlin, et al.
Sinclar, et al., "Hyperspectral confocal microscope," 2006, Applied Optics, vol. 45, No. 24, pp. 6283-6291.

(Continued)

*Primary Examiner* — Kiho Kim
(74) *Attorney, Agent, or Firm* — Marcus S. Simon

(57) ABSTRACT

A hyperspectral stimulated emission depletion ("STED") microscope system for high-resolution imaging of samples labeled with multiple fluorophores (e.g., two to ten fluorophores). The hyperspectral STED microscope includes a light source, optical systems configured for generating an excitation light beam and a depletion light beam, optical systems configured for focusing the excitation and depletion light beams on a sample, and systems for collecting and processing data generated by interaction of the excitation and depletion light beams with the sample. Hyperspectral STED data may be analyzed using multivariate curve resolution analysis techniques to deconvolute emission from the multiple fluorophores. The hyperspectral STED microscope described herein can be used for multi-color, subdiffraction imaging of samples (e.g., materials and biological materials) and for analyzing a tissue by Förster Resonance Energy Transfer ("FRET").

22 Claims, 3 Drawing Sheets

(56) References Cited

OTHER PUBLICATIONS

Jones, et al., "Weighting hyperspectral image datea for improved multivariate curve resoltion results," 2008, Journal of Chemometrics, vol. 22, pp. 482-490.

Vermaas et al,. "In vivo hyperspectral confocal fluorescence imaging to determine pigment localization and distribution in cyanobacterial cells," Proc. Natl. Acad. Sci. U S A. Mar. 11, 2008;105(10):4050-5.

Aaron, et al., "Imaging of Protein Reorganization and Interactions at the Nanoscale," presented at at Sixth Annual NIH Directors Pioneer Symposium Sep. 30-Oct. 1, 2010.

Shi, et al., "Superlocalization Spectral Imaging Microscopy of a Multicolor Quantum Dot Complex," *Anal. Chem.*, 2012, 84 (3), pp. 1504-1509.

Jones, et al., "Preprocessing strategies to improve MCR analyses of hyperspectral images," 2012, Chemometrics and Intellegent Laboratory Systems.

\* cited by examiner

HYPERSPECTRAL STIMULATED EMISSION DEPLETION MICROSCOPY AND METHODS OF USE THEREOF

STATEMENT OF GOVERNMENT RIGHTS

This invention was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

BACKGROUND

Fluorescence microscopy is widely used in molecular and cell biology and other applications for non-invasive, time-resolved imaging. Despite these advantages, standard fluorescence microscopy is not useful for ultra-structural imaging, due to the optical diffraction limit. The optical diffraction limit is a physical property that limits the resolution of conventional microscope systems. Due to its wave properties, light passing through a circular lens creates a ring-shaped diffraction pattern; the images of two different points formed by such a lens can be resolved if the principal diffraction maximum of one point lies outside of the first minimum of the other point. This theoretical diffraction limit, is approximately equal to $0.61 \cdot \lambda/NA$, where $\lambda$ is the wavelength of the light and NA is the numerical aperture of the lens, given by $$NA = n \cdot \sin \alpha \quad \text{(Formula I)}$$

where n is the index of refraction of the optical medium between the lens and the specimen and $\alpha$ is the half-angle of acceptance of the lens. Currently available microscope objective lenses typically have NA<1.4, so that the theoretical diffraction limit for visible light is >200 nm; in practice the resolution limit of standard optical microscopes, compromised by various lens aberrations, is poorer, seldom much below 500 nm.

Over the past several years, a number of new technical innovations have been introduced that effectively circumvent the optical diffraction limit, opening the door to vastly improved fluorescence microscopy image resolution. The first of these techniques, termed Stimulated Emission Depletion ("STED") microscopy, relies on a fluorescence excitation source coupled to a second illumination beam that prevents fluorescence relaxation of all but a small volume of fluorophores in the sample, thereby greatly enhancing image resolution. The second depletion beam used in STED acts to force an excited fluorophore to the ground state by stimulated emission. As such, a spectrally distinct signature is produced that is separable from the fluorescence emitted from molecules that have not undergone the depletion process.

In order to achieve spatial separation between the two processes, the second depletion beam is phase-shaped such that it produces an optical vortex at the sample—rendering a very small (typically 30-50 nm across) point at the center of the vortex that is sufficiently free of depletion energy. This "depletion-free" zone allows only a small, sub-diffraction volume of fluorophores to be detected. Subsequent raster scanning of the coupled excitation/depletion beams can then be used to assemble an image with greatly enhanced detail.

While representing a monumental advance in the field of molecular imaging, STED microscopy retains some important limitations. Firstly, the system complexity and cost is formidable. Original STED systems consisted of two mode locked femtosecond pulsed laser sources that required sophisticated synchronization in order to assure that the excitation and depletion laser pulses reached the sample within less than 100 picoseconds of each other. The introduction of a super-continuum based STED system has reduced this burden. However, most STED imaging systems still rely on a single excitation and single depletion beam. This generally limits STED to the detection of a single fluorophore in the sample. While multi-color STED systems have been demonstrated, they require the use of multiple (and synchronized) pulsed laser sources as described above, thereby preventing practical implementation in nearly any biological research settings.

Accordingly, new techniques capable of multiplexed detection are needed to harness the benefits of fluorescence microscopy for ultra-resolution imaging of biological and other samples.

SUMMARY

Molecular imaging is arguably most useful when used to establish relationships between two or more structures in a sample. The present disclosure relates to apparatuses and methods for multi-color, subdiffraction imaging using hyperspectral stimulated emission depletion microscopy ("hyperspectral STED" or "HSTED"). HSTED combines the increased resolving power of stimulated emission depletion microscopy ("STED") with spectral (e.g., multi-wavelength) imaging. The HSTED apparatuses and methods described herein require only a single pulsed laser source and no complex pulse synchronization system(s), greatly reducing barriers to implementation.

In one embodiment, a hyperspectral STED microscope system includes a light source, optical systems for generating an excitation light beam and a depletion light beam, optical systems for focusing the excitation and depletion light beams on a sample, and systems for collecting and processing data generated by interaction of the excitation and depletion light beams with the sample.

In one embodiment, a method for multi-color, subdiffraction imaging of a three-dimensional space is described. The method includes (1) providing a sample that includes a three-dimensional space having one or more features of interest that are at least one of (a) smaller than an optical diffraction limit or (b) separated by a distance that is less than the optical diffraction limit, (2) labeling the three-dimensional space with two or more different fluorophores having spectrally overlapped excitation and emission wavelengths, and (3) positioning the sample in a hyperspectral stimulated emission depletion microscope system that is configured to generate an excitation light beam and a depletion light beam that is substantially coincident with the excitation light beam. The method further includes (4) illuminating an optical section of the three-dimensional space with the excitation light beam and the depletion light beam to excite fluorescence emission from the two or more different fluorophores in the optical section and, substantially simultaneously, depleting emission from substantially all but a selected subset of the two or more different fluorophores in the optical section, (5) collecting polychromatic fluorescence emission data from the spectrally distinct emission of each of the two or more different fluorophores, and (6) processing the polychromatic fluorescence emission data to identify and localize the fluorescent emission from each of the two or more different fluorophores.

In another embodiment, a method for multi-color subdiffraction imaging of a biological sample is disclosed. The method includes (1) labeling a tissue with two or more different fluorophores having spectrally overlapped excitation and emission wavelengths, (2) illuminating an optical section of the tissue with an illuminating light source to excite fluorescence emission from the two or more different fluorophores in the optical section and, substantially simultaneously, depleting emission from substantially all but a selected subset of the two or more different fluorophores in the optical section, (3) collecting polychromatic fluorescence emission data from each of the spectrally distinct two or more different fluorophores in the optical section; and (4) processing the polychromatic fluorescence emission data to identify and localize the fluorescent emission from each of the two or more different fluorophores.

The methods described above may further include collecting fluorescence emission data from a multitude of optical sections of the sample, and assembling the fluorescence emission data from the multitude of optical sections to produce a three-dimensional, high-resolution image of the sample.

In yet another embodiment, a method for analyzing a tissue by Förster Resonance Energy Transfer ("FRET") is described. The method includes (1) labeling a sample with at least one FRET pair, the at least one FRET pair comprising a donor fluorophore labeling a first structure and an acceptor fluorophore labeling a second structure, (2) illuminating at least a first optical section of the sample with an illuminating light source to fluorescently excite donor fluorophores in the optical section and, substantially simultaneously, depleting emission from substantially all but a selected subset of the donor fluorophores in the optical section, and (3) collecting polychromatic fluorescence emission data from a multitude of optical sections of the sample. The polychromatic fluorescence emission data may include one or more of (i) fluorescent emission from undepleted donor fluorophores that are not in proximity to an acceptor fluorophore, (ii) fluorescent emission from acceptor fluorophores that are in proximity to undepleted donor fluorophores, or (iii) both.

The method further includes (4) processing the polychromatic fluorescence emission data to identify and localize the fluorescent emission from each of the donor fluorophores and the acceptor fluorophores, and (5) assembling the fluorescence emission data from the multitude of optical sections to produce a three-dimensional, high-resolution map of the proximity of the first structure to the second structure.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

DETAILED DESCRIPTION

I. Introduction

Figure 1:
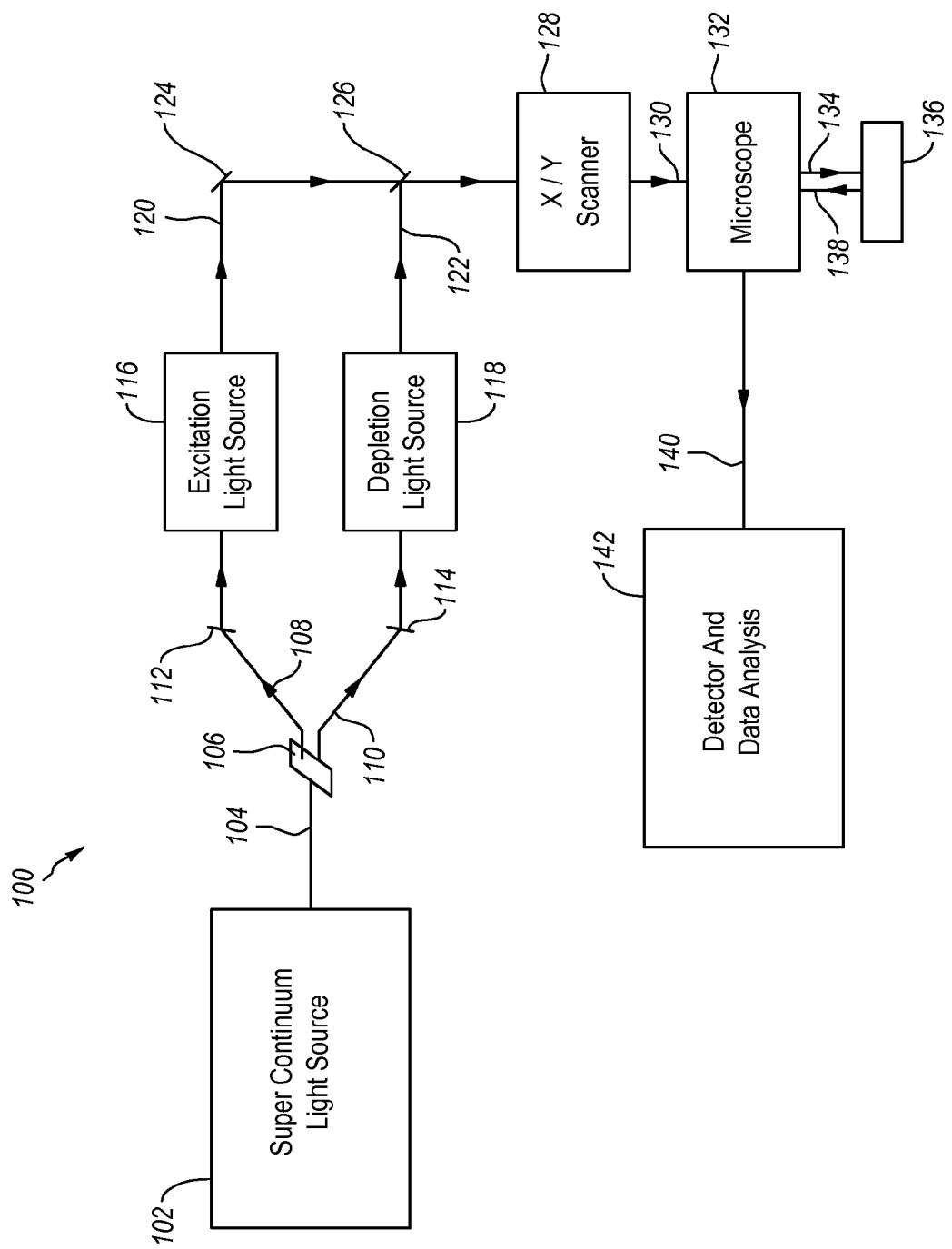
FIG. 1 illustrates a block diagram of a hyperspectral STED microscope system according to an embodiment.

Molecular imaging can be useful for establishing relationships between two or more structures in a sample. The present disclosure relates to apparatuses and methods for multi-color, subdiffraction imaging using hyperspectral stimulated emission depletion microscopy ("hyperspectral STED" or "HSTED"). HSTED combines the increased resolving power of stimulated emission depletion microscopy ("STED") with spectral imaging. The HSTED apparatuses and methods described herein require only a single pulsed laser source and no complex pulse synchronization system(s), thereby greatly reducing barriers to implementation.

An embodiment of an HSTED system that can be used to practice the methods described herein may include (i) a supercontinuum light source configured to generate broadband, coherent illumination light suitable for sub-diffraction imaging of two or more different fluorophores, (ii) a beam splitter downstream from the supercontinuum light source, wherein the beam splitter is configured to split an incoming light beam from the supercontinuum light source into a first beam path and a second beam path, (iii) an excitation light beam formed from the first beam path, (iv) a depletion light beam formed from the second beam path, and (v) optics configured to focus the excitation light beam and the depletion light beam on a selected region of a sample. The excitation light beam is configured to substantially simultaneously excite fluorescence from the two or more different fluorophores and the depletion light beam is configured to deplete fluorescence from essentially all but a selected subset of the two or more different fluorophores. The HSTED system further includes a detector positioned to detect fluorescence from the sample and a data analysis system configured to control data acquisition from the sample and analyze fluorescence data obtained from the sample.

The ability of hyperspectral STED to discriminate multiple fluorophores substantially simultaneously depends on collection of both spatially- and spectrally-resolved information from the sample. This is accomplished by spatially scanning (e.g., optical sectioning) the sample, raster scanning the excitation and depletion beams, and by incorporating a spectrometer in the microscope's detection path. The spectral information in each optical section (e.g., a pixel or voxel) contains contributions from all fluorophores that are present at that location; the spatial information can be used to help extract the contribution of each of the fluorophores, provided that such components are not present in the same ratio relative to each other in all optical sections. Chemometric analysis techniques, such as multivariate curve resolution ("MCR"), may then be applied to deconvolute the contribution from each fluorophore, thereby allowing the collection and processing of hyperspectral STED data. Subsequently, data from each of the optical sections can be combined to produce a high-resolution (i.e., better than the optical diffraction limit), multi-color image of the sample.

II. Hyperspectral Sted Systems

Referring now to FIG. 1, an embodiment of a hyperspectral STED system 100 is schematically illustrated. The hyperspectral STED system 100 can be used practice the methods described hereinbelow.

The hyperspectral STED system 100 includes a supercontinuum light source 102 configured to generate a broadband, coherent illumination light beam 104 suitable for sub-diffraction imaging of two or more different fluorophores. The supercontinuum light source 102 emits pulses of light with each pulse having a duration of about 80 picoseconds ("ps") (i.e., $100 \times 10^{-12}$ seconds) to about 150 ps (e.g., about 100 ps). As will be explained in greater detail below, the supercontinuum light source 102 includes a number of components configured to emit an intense, polychromatic light beam having a substantially continuous spectrum (e.g., from about 400 nm to about 800 nm), which more-or-less covers the visible light spectrum.

The light beam 104 generated by the supercontinuum light source 102 is split into a first light beam 108 and a second light beam 110 by a beam splitter 106. Depending on the configuration of the beam splitter 106, the light may be split between the first and second light beams 108 and 110 essentially equally or at some other ratio. Following splitting, the first and second light beams 108 and 110 may be redirected by a number of mirrors (e.g., mirrors 112 and 114). The first light beam is manipulated by the illustrated excitation light source 116 to yield an excitation light beam 120. Likewise, the second light beam is manipulated by the illustrated depletion light source 118 to yield a depletion light beam 122. Alignment mirrors 124 and 126 render beams substantially coaxial, and telecentric. The illustrated X/Y scanner 128 raster scans the beams 120 and 122 onto the microscope 132 to focus the excitation and depletion light beams 120 122 on a selected region of a sample 136. Alignment of the mirrors 124 and 126 enables the excitation light beam 120 and the depletion light beam 122 to be in phase in order to avoid the possibility of deleterious destructive interference between the two light beams. Likewise, given the length of the light pulses (i.e., about 100 ps) and the time course of fluorescence, the beams 120 and 122 should impinge on the sample within about 5-10 ps of one another to avoid the scenario where the excited fluorophores emit before they can be depleted by the depletion light beam.

The excitation light beam 120 is configured to substantially simultaneously excite fluorescence from the two or more different fluorophores in the sample 136 and the depletion light beam 122 is configured to deplete fluorescence from essentially all but a selected subset of the two or more different fluorophores. For example, the depletion light beam 122 may be torus-shaped with a depletion zone that substantially surrounds a zone of essentially zero intensity in the center of the depletion light beam 122 (i.e., an optical vortex or a zone of zero intensity at the center of the torus). Such a torus-shaped depletion zone will deplete fluorescence from the fluorophores excited by the excitation light beam 120 in essentially all but a center portion of the torus-shaped depletion zone.

The undepleted fluorophores excited by the excitation light beam emit a fluorescent signal 138 that is focused by the microscope 132 and directed to a detection and data analysis system 140. The detection and data analysis system 140 includes a detector positioned to detect fluorescence 138 from the sample 136 and a data analysis system configured to control data acquisition from the sample 136 and analyze fluorescence data obtained from the sample.

Figure 2:
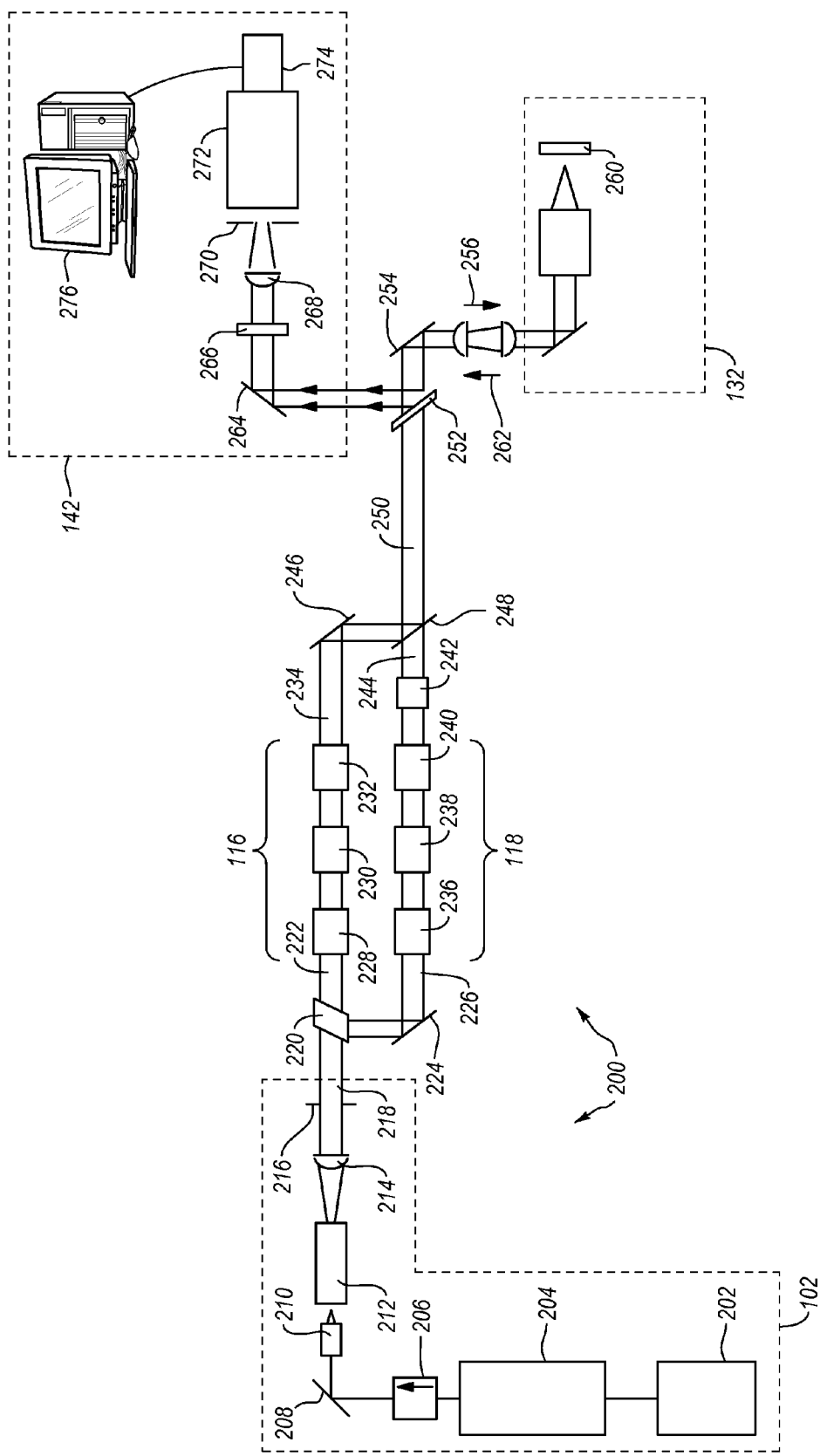
FIG. 2 illustrates another diagram of a hyperspectral STED microscope system according to an embodiment.

Referring now to FIG. 2, a more detailed embodiment of a hyperspectral STED system 200 is schematically illustrated. The hyperspectral STED system 200 includes essentially the same components that were discussed in reference to FIG. 1. For clarity sake, a number of multi-component systems that were discussed generally in reference to FIG. 1 are labeled with their FIG. 1 numbers.

The supercontinuum light source 102 illustrated in FIG. 2 includes a pump laser 202 that feeds a Ti:sapphire laser 204. The Ti:sapphire laser produces pulses of light, such as ~100-200 femtoseconds in length at a power greater than 1 W. To generate broadband coherent illumination, the Ti:sapphire laser 204 is coupled to a photonic crystal fiber 212 ("PCF"). The Ti:sapphire laser 204 is coupled to the PCF 212 through an optical isolator 206, a mirror 208, and a focusing lens 210.

The optical isolator prevents back reflection of the light from the Ti:sapphire laser 204 that can disrupt mode locking. The PCF 212 generates multiple non-linear effects (i.e. fluorescence, Raman, stimulated Raman, etc.) to form a broadband light source of approximately, for example, 400-800 nm.

Light from the PCF passes through a lens 214 and a slit 216 to form an incident light beam 218 (or light pulses having a duration of, for example, about 100 ps) that is passed into beam splitter 220. The beam splitter 220 splits the incident light beam 218 into a first light beam 222 and a second light beam 226. In the illustrated embodiment, the beam splitter 220 is a polarization beam splitter. However, other types of beam splitters may be employed. The polarization beam splitter functions because the incident light 218 from the supercontinuum light source 102 is polarized at about 45 degrees. The beam splitter 220 splits the incident light 218 into substantially perpendicular (90 degrees) and perpendicular parallel (0 degrees) components. This configuration provides roughly equal power in the first light beam 222 and a second light beam 226 and allows the beams 222 and 226 to be efficiently recombined later.

The first light beam 222 is altered by the excitation light source 116 to generate excitation light beam 234. In the illustrated embodiment, the excitation light source 116 includes a monochrometer 228 that is used to select a small wavelength range of wavelengths (e.g., about 100 nm) from the first light beam 222 using rotating prisms and slits. A beam expander 230 is needed to enlarge beam for scanning into the microscope. A cylindrical zoom lens 232 is used to correct for beam asymmetry and astigmatism due to prism dispersion.

The second light beam 226 is altered by the depletion light source 118 to generate depletion light beam 244. In the illustrated embodiment, the depletion light source 118 includes a monochrometer 236, a beam expander 238, and a cylindrical zoom lens 240.

Additionally, the depletion light source 118 includes a spiral phase plate 242 that is used to generate the torus-shaped depletion light beam. The spiral phase plate 242 includes optical devices that twist incoming light like a corkscrew around its axis of travel. Because of the twisting, the light waves at the axis cancel each other out. This corkscrew of light, with darkness at the center, is called an optical vortex. When projected onto a flat surface, the optical vortex looks like a ring of light, with a dark hole in the center. This dark hole is a region of essentially zero intensity.

Alignment mirrors 246 and dichroic beam splitter 248 combine the beams into beam combined 250. Combined beam 250 includes the excitation light beam 234 and the depletion light beam 244. The combined beam 250 is passed through double dichroic beam splitter 252 to separate excitation and emission and depletion. The combined beam 250 then hits the X/Y scanner 254 to raster scan the combined beam 250 into the microscope 132, which focuses the combined beam 250 on a selected region of a sample 260. Incoming light (i.e., the combined beam 250) going into the microscope 132 is illustrated at 256.

When the excitation light beam 234 is irradiated onto a region of the sample 260 that contains molecules of a fluorophore, the excitation light beam 234 can excite the fluorophore molecules to emit light. The region of the sample irradiated by the excitation light beam 234 is diffraction limited. Nevertheless, a STED microscope can break through the optical diffraction barrier and achieve great enhancements in resolution by depleting the fluorescence from excited fluorophore molecules in all but a center portion of the illuminated region. This is accomplished with the depletion light beam 244.

When the depletion light beam 244 is irradiated onto the sample 260 essentially simultaneously with the excitation light beam 234, the excited fluorophore molecules that are irradiated by the depletion light beam 244 are forced to relax to the ground state rather than emitting a fluorescence photon. Fluorophores can, therefore, be "switched off" by irradiation with the depletion light beam 244. Using an intense depletion light beam 244 causes almost all of the excited molecules to return to the ground state, leaving only the region of the sample very close to the center of the excitation spot excited.

The undepleted spot at the center of the irradiated zone is not diffraction limited and the resolution (i.e., the size of the undepleted spot) is generally limited only by the power of the depletion light beam 244. However and in addition, while the size of the undepleted zone can be made as small as theoretically possible, the ability to collect a fluorescence signal from the undepleted zone is limited by the number of excitation photons incident on the sample and the bleaching time of the fluorophore(s).

Fluorescence from the remaining excited dye molecules is then redirected by the optics of the microscope 132 (the outgoing fluorescent signal is indicated at arrow 262). Outgoing fluorescent signal 262 is redirected by the X/Y scanner 254 and isolated by the double dichroic beam splitter 252. The fluorescent signal 262 is the reflected by mirror 264, passed through an edge filter 266 to remove any excitation light that was inadvertently reflected through the detection path, and sent through a focusing lens 268 and a confocal pinhole 270 for optical sectioning. In-focus light enters a spectrometer 272 with dispersive element such as a grating or prism and the signal is dispersed onto an ultra-sensitive EMCCD detector 274 and spectra are read-out at each voxel in the image. The computer depicted at 276 controls EMCCD 274 acquisition, in synchronization with the X/Y scanner 254 and z-position of the sample 260 to optically section the sample 260 for collection of data for construction of a composite image of all or a portion of the sample 260.

Figure 3:
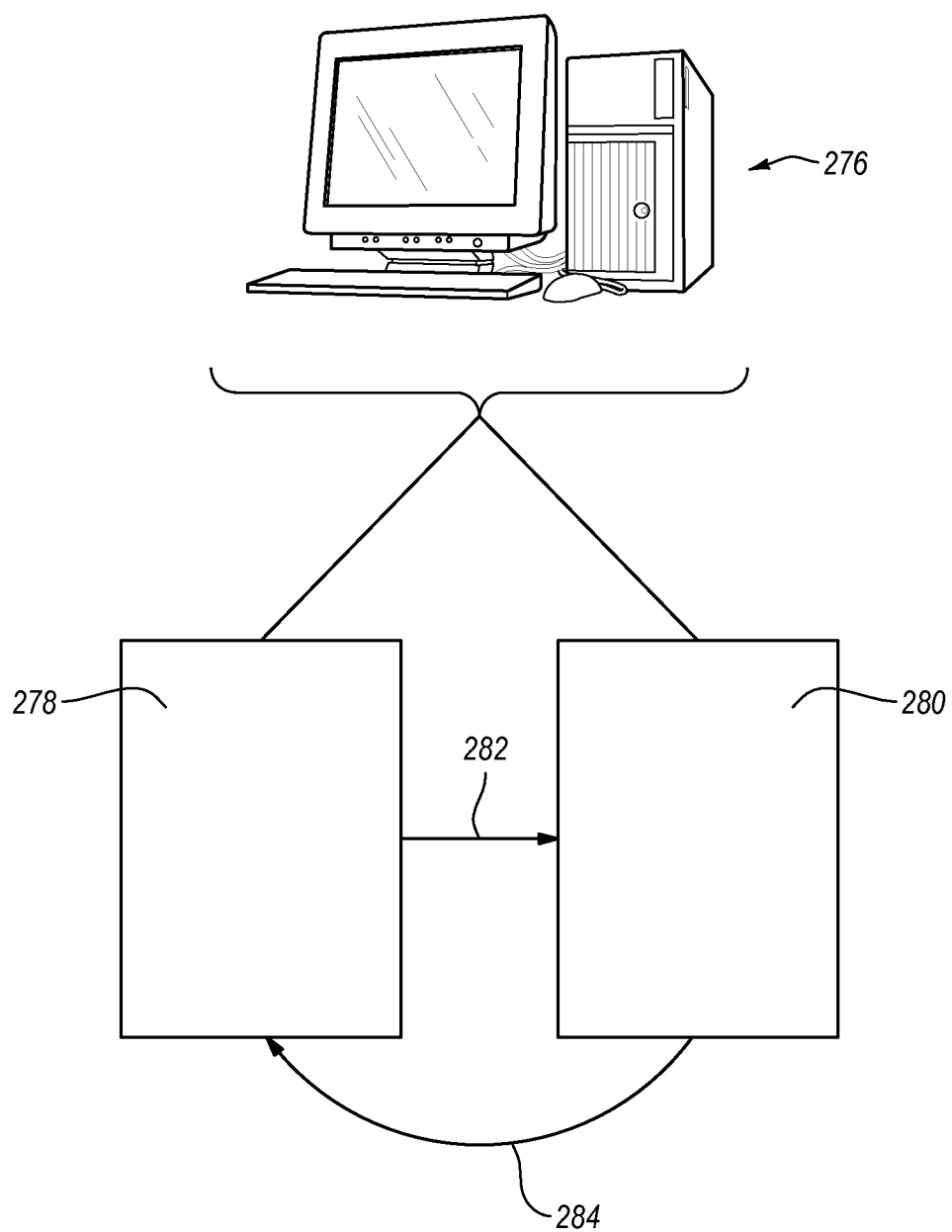
FIG. 3 schematically illustrates a computing system for receiving and processing data from a hyperspectral STED microscope system according to an embodiment.

Referring now to FIG. 3, computer 276 is illustrated in greater detail. Computer 276 includes memory modules 278, processing modules 280, and communication modules 282 and 284 that allow the memory modules 278 and the processing modules 280 to communicate with one another. For instance, the memory modules 278 include control modules and data acquisition modules that include instructions that are read and executed by the processing modules 280 and may be used to control acquisition of data from HSTED system 200 of FIG. 2. For example, as stated above, the control modules may be used to control EMCCD data acquisition, in synchronization with the X/Y scanner and z-position of the sample to optically section the sample. Data from individual voxels is collected and stored in the memory module 278. Data from a multitude of voxels may be collected, stored, and processed for construction of a composite image of all or a portion of the sample. The control modules may include computer executable instructions stored thereon that can be executed by the processing modules 280 for executing the methods described hereinbelow.

Processing modules 280 may receive programming instructions (e.g., computer executable instructions) from the memory modules 278 that may be used to control EMCCD data acquisition, in synchronization with the X/Y scanner and z-position of the sample to optically section the sample. The computer executable instructions from the memory modules 278 may also be used to control the rate of data acquisition, the range of wavelengths transferred from the spectrometer and collected by the EMCCD, and the like. The processing modules 280 may also receive data from the memory modules 278 for data processing according to computer executable instructions received from the memory modules 278. The processing modules 280 may include preprocessing modules for, for example, compressing and binning of data stored in the memory modules 278. Likewise, the processing modules a series of data analysis modules. These include preprocessing modules for preprocessing selected terms in the data to aid in analysis and multivariate curve resolution ("MCR") modules.

MCR is a so-called chemometric technique that allows the spectral contributions of many fluorophores in mixtures to be teased apart. These approaches are often called self-modeling mixture analysis, blind source/signal separation, and spectral unmixing. For example, from a data set comprising fluorescence spectra from a series of samples each containing multiple fluorophores at varying abundances, multivariate curve resolution methods can be used to extract the fluorescence spectra of the individual fluorophores, along with their relative abundances in each of the samples, essentially unmixing the total fluorescence spectrum into the contributions from the individual components.

The memory modules 278 may further include storage modules for processed data (e.g., processed voxels and/or processed "bins" of data). The processing modules 280 may further include modules for assembly of the individual voxels into a composite, high-resolution image of the sample and visualization modules for displaying the composite image on, for example, the serene of computer 276.

MCR analysis and description of various computer programs for MCR analysis have been covered in detail elsewhere and will not be covered in detail here. Additional discussion of MCR analysis and description of various computer programs for MCR analysis can be found in H. D. T. Jones et al., Preprocessing strategies to improve MCR analyses of hyperspectral images, Chemometr. Intell. Lab. Syst. (2012), DOI: 10.1016/j.chemolab.2012.01.011 (Available online 2 Feb. 2012, In Press), and U.S. Pat. Nos. 6,675,106, 6,584,413, 7,451,173, 7,400,772, 7,283,684, 7,725,517, 7,472,153, 6,415,233, 6,341,257, 6,711,503, 6,687,620, 6,842,702, 6,922,645, the entireties of which are incorporated herein by reference. Briefly, however, MCR analysis generally involves assembling the data into a data matrix of individual spectra, defining the noise contribution in the data, setting the number of MCR iterations to be performed, providing an estimate of the number of fluorophores present in the data set, and providing the MCR analysis algorithm with spectra for the fluorophores. The MCR algorithm in the processing modules 280 includes constrained least squares analysis modules and classical least squares modules I fitting the data and teasing apart the spectra according to the above described model.

However, the problem may be poorly resolved due to rotational ambiguity (many possible solutions can equivalently represent the measured data). As a result, additional constraints are generally used such as non-negatively, unimodality, or known interrelationships between the individual components (e.g., kinetic or mass-balance constraints). In the present case, the fluorophores used to label a sample and their unique spectral signatures are generally known. Likewise, because not all voxels in a sample will contain the same fluorophores in the same concentrations, voxels can be compared and the comparison can be used to determine the contribution of individual fluorophores.

While HSTED data has not been collected and processed with MCR, the article by Jones et al., which was incorporated by reference above, describes methods for analysis of hyperspectral confocal microscopy data. While HSTED data is expected to be different than hyperspectral confocal microscopy data in a number of respects, the methods described in Jones et al. are expected to be adaptable to HSTED data. For example, Jones et al. describes the determination and removal of noise sources from hyperspectral confocal data. Noise sources in HSTED data may include, but are not limited to, detector noise (cosmic spikes, detector offset, dark current, EMCCD gain noise, structured noise), Poisson noise originating from the signal itself, and noise from the laser due to variations in power.

Jones et al. also describes the handing of hyperspectral data. Changes that are expected to be necessary for adapting the analysis software described in Jones et al. for hyperspectral STED are expected to include, but are not limited to, file I/O, the files will be in a different format and with different data structure and this will need to be accommodated by existing software; data compression, the files have potential to contain more pixels than previous imaging and though sophisticated data compression routines exist they will need to be made flexible enough to incorporate the data from the hyperspectral STED microscope. The compression can occur as an intermediate processing step and, once a spectral model has been developed describing the image data, the model can be applied to the uncompressed data using a classical least squares approach to predict the results at full spatial resolution.

III. Methods for Multi-Color, Subdiffraction Imaging

In one embodiment, a method for multi-color, subdiffraction imaging of a three-dimensional space is described. Embodiments of a hyperspectral STED system that can be used to practice the methods described herein are described in detail in reference to FIGS. 1-3. The method includes (1) providing a sample that includes a three-dimensional space having one or more features of interest that are smaller than an optical diffraction limit, and (2) labeling the three-dimensional space with two or more different fluorophores having spectrally overlapped excitation and emission wavelengths. In general, the different fluorophores used as labels do not need to be spectrally distinct in order to be resolved according to the methods described herein. Instead, emission spectra for labeling fluorophores can be substantially overlapped and still be distinguished so long as there is some characteristic that allows the spectra to be distinguished from one another. For example, spectra may be distinguished if their relative abundance is different in different pixels, if their emission maxima are separated by 2 nm or more, or if they have a shape change in their emission spectra (e.g., a difference in rise/fall, an extra bump, etc.). In one embodiment, the labeled samples discussed herein may be labeled with two or more different fluorophores having spectrally overlapped excitation wavelengths and spectrally distinct emission wavelengths. However, as explained above, it is not a requirement that the emission wavelengths of the fluorophores be spectrally distinct in all cases.

The method further includes (3) positioning the sample in a hyperspectral stimulated emission depletion microscope system that is configured to generate an excitation light beam and a depletion light beam that is substantially coincident with the excitation light beam, (4) illuminating an optical section of the three-dimensional space with the excitation light beam (e.g., excitation light beam 120 of FIG. 1) and the depletion light beam (e.g., depletion light beam 122 of FIG. 1) to excite fluorescence emission from the two or more different fluorophores in the optical section and, substantially simultaneously, depleting emission from essentially all but a selected subset of the two or more different fluorophores in the optical section, (5) collecting polychromatic fluorescence emission data from the spectrally distinct emission of each of the two or more different fluorophores, and (6) processing the polychromatic fluorescence emission data to identify and localize the fluorescent emission from each of the two or more different fluorophores. The collecting and processing steps of the above recited method may be executed with the X/Y scanner 128, microscope 132, and the detector and analysis system 142 described in reference to FIG. 1.

In another embodiment, a method for multi-color subdiffraction imaging of a biological sample is disclosed. The method includes (1) labeling a tissue with two or more different fluorophores having spectrally overlapped excitation and emission wavelengths, (2) illuminating an optical section of the tissue with an illuminating light source to excite fluorescence emission from the two or more different fluorophores in the optical section and, substantially simultaneously, depleting emission from essentially all but a selected subset of the two or more different fluorophores in the optical section, (3) collecting polychromatic fluorescence emission data from each of the spectrally distinct two or more different fluorophores in the optical section; and (4) processing the polychromatic fluorescence emission data to identify and localize the fluorescent emission from each of the two or more different fluorophores.

The methods described above may further include collecting fluorescence emission data from a multitude of optical sections of the sample, and assembling the fluorescence emission data from the multitude of optical sections to produce a three-dimensional, high-resolution image of the sample. In one example, collecting fluorescence emission data from a multitude of optical sections of the sample, and assembling the fluorescence emission data from the multitude of optical sections to produce a three-dimensional, high-resolution image of the sample may be accomplished with the computer 278 described in reference to FIG. 3.

As discussed in greater detail elsewhere herein, the depletion light source used in the methods described herein includes a torus-shaped depletion zone that is configured to deplete fluorescence from the two or more different fluorophores in all but a center portion of the torus-shaped depletion zone. As discussed in greater detail elsewhere herein, the illuminating step comprises transmitting incident light from a supercontinuum light source having an emission range of about 400-800 nm and further includes selecting a wavelength or a range of wavelengths from the supercontinuum light source to excite fluorescence and depletion from the two or more different fluorophores.

As discussed in greater detail elsewhere herein, the detection path includes a spectrometer, which permits collection of a complete emission spectrum for all of the fluorophores present in each optical section of a sample (e.g., a three-dimensional space or a tissue sample).

In one embodiment, the sample includes one or more features of interest that smaller than an optical diffraction limit and/or separated by a distance that is less than the optical diffraction limit. In one embodiment, a first feature of interest can be labeled with a first fluorophore and a second feature of interest can be labeled with a can be labeled with a second different fluorophore. As discussed in greater detail elsewhere herein, because of the unique characteristics of STED or HSTED, objects that are smaller than the optical diffraction limit or that are separated by a distance that is less than the optical diffraction limit can be resolved. This is in contrast to conventional light microscopy.

HSTED can be used for multi-color, high-resolution imaging and analysis of a wide variety of inorganic and biological materials. Suitable areas of application for HSTED microscopy, as described herein, include, but are not limited to, materials sciences and geosciences (e.g., metals and manufactured silicon materials, detection of inclusions, composition changes, interfacial distributions, material component degradation, etc.). nanomaterials (e.g., biomedical applications, composition, characterization of, etc.) and the biological sciences (e.g., visualization and characterization of subcellular organelles). Suitable examples of biological samples include, but are not limited to, prokaryotic cells (e.g., bacteria), eukaryotic cells (e.g., individual human cells or human tissues), a fixed and sectioned tissue, a fixed and sectioned cell, a bacterium, or a virus. Because multiple structures in a cell can be labeled and imaged simultaneously and because the illumination is not destructive, in many embodiments the tissue may be a living tissue. Imaging of living tissue may be particularly attractive because biological processes and the proximity of structures to one another can be viewed dynamically instead of observing structures in a fixed tissue.

In one embodiment, the two or more different fluorophores have excitation and depletion wavelengths within a range of about 20-50 nm. Suitable examples fluorophores include, but are not limited to organic dyes, fluorescent proteins, and naturally occurring fluorophores.

Suitable examples of organic dyes that can be used with the HSTED systems and methods described herein include, but are not limited to, the Alexa Fluor dyes available from Life Technologies and the Atto Tec dyes available from ATTO-TEC GmbH. The Alexa Fluor dyes and the Atto Tec dyes each include dyes having absorption maxima ranging from about 350 nm to about 785 nm. By way of example and not limitation, the range of Alexa Fluor dyes is illustrated below in Table 1.

TABLE 1

| Alexa Fluor dye | Absorption max. (nm) | Emission max (nm) | Emission color |
| --- | --- | --- | --- |
| Alexa Fluor 350 | 346 | 442 | Blue |
| Alexa Fluor 405 | 401 | 421 | Blue |
| Alexa Fluor 430 | 433 | 541 | Green/Yellow |
| Alexa Fluor 488 | 496 | 519 | Green |
| Alexa Fluor 532 | 532 | 553 | Yellow |
| Alexa Fluor 546 | 556 | 573 | Orange |
| Alexa Fluor 555 | 555 | 565 | Orange |
| Alexa Fluor 568 | 578 | 603 | Orange/Red |
| Alexa Fluor 594 | 590 | 617 | Red |
| Alexa Fluor 610 | 612 | 628 | Red |
| Alexa Fluor 633 | 632 | 647 | Far Red |
| Alexa Fluor 635 | 633 | 647 | Far Red |
| Alexa Fluor 647 | 650 | 665 | Near-IR |
| Alexa Fluor 660 | 663 | 690 | Near-IR |
| Alexa Fluor 680 | 679 | 702 | Near-IR |
| Alexa Fluor 700 | 702 | 723 | Near-IR |
| Alexa Fluor 750 | 749 | 775 | Near-IR |
| Alexa Fluor 790 | 784 | 814 | Near-IR |

While the Alexa Fluor dyes and the Atto Tec dyes are good examples of organic dyes, there are numerous other commercially available organic dyes covering many different ranges of absorption and emission maxima.

In addition to organic dyes, fluorescent proteins, some naturally occurring fluorophores can also be used, and even autofluorescent molecules in the cell/tissue/Material. While fluorescent proteins are generally not as bright or as efficient as organic dyes, their specificity makes them attractive. Examples of available fluorescent protein include cyan fluorescent protein, green fluorescent protein, yellow fluorescent protein, orange fluorescent protein, red fluorescent protein, and far-red fluorescent protein. Naturally occurring fluorophores that may be used include, but are not limited to, chlorophylls, phycobilins, and carotenoids.

In one embodiment, the sample may be labeled with two to four, two to seven, two to ten, or even more different fluorophores. Because of the capabilities of the HSTED system coupled with MCR analysis, the different fluorophores may have spectrally overlapped excitation wavelengths and spectrally distinct emission wavelengths or spectrally overlapped excitation and emission wavelengths. W. F. Vermaas et al., In vivo hyperspectral confocal fluorescence imaging to determine pigment localization and distribution in cyanobacterial cells, Proc. Natl. Acad. Sci. USA. 2008 Mar. 11; 105 (10): 4050-5, the entirety of which is incorporate herein by reference, describes the use of MCR analysis of conventional resolution microscopy data to resolve and colocalize six different naturally occurring fluorophores in cyanobacterial cells. In unpublished data from the inventor, MCR analysis of conventional resolution microscopy data could be used to resolve seven different dyes. The dyes were Alexa Fluor 488, Alexa Fluor 514, Alexa Fluor 532, Alexa Fluor 546, Alexa Fluor 555, Alexa Fluor 568, and rhodamine. However, it does not appear that 7 dyes is the practical upper limit. The number of dyes used simultaneously can go higher. Resolving dyes in a labeled sample is dependent on a number of parameters, with three important parameters being 1) spectral overlap of the dyes or autofluorescence, 2) spatial overlap (are they in the same pixel or voxel?), and 3) the relative concentrations or relative spectral contribution of the fluorophores. For instance, resolution of fluors is much more difficult if one fluorophore is super bright and another collocated is very dim. The instrument parameters also weigh heavily into this. For example, the number of spectral channels, the size of the pixels, and the instrument noise are all important. Substantially overlapping dyes can be resolved with MCR even when the peak emissions are atop one another provided that a shape change exists in the spectral signature and the components differ in relative abundances throughout the image data set—i.e., they cannot be completely colocalized and at the same ratios in every pixel or voxel in the data set. If the spectral shapes are similar, then approximately 2-5 nm separation in the emission maxima is needed in order to resolve the dye signals. The same requirements for relative intensity changes throughout the image data set exist in any case.

In yet another embodiment, a method for analyzing a tissue by Förster Resonance Energy Transfer ("FRET") is described. FRET is a well-known technique that is often used in the life sciences and other areas to determine the proximity of a first structure labeled with a first fluorophore (i.e., the donor) to another structure that is labeled with a second, compatible fluorophore (i.e., the acceptor). When there is overlap between the emission spectrum of the donor and the excitation spectrum of the acceptor and they are in close proximity (e.g., typically less than about 10-20 nm) to one another, the donor may transfer its energy to the acceptor non-radiatively through dipole-dipole coupling.

However, the complexity of this approach is magnified when attempted within the milieu of a living cell under imaging conditions. This is because the length scale at which FRET occurs is more than an order of magnitude smaller than conventional optical resolution. Therefore, measurement of biomolecular assemblies is inherently uncertain when imaging FRET. This is primarily due to the following: when a FRET measurement is made, the resulting donor fluorescence is a function of both the average donor-acceptor separation distance, as well as the total number of donors within the excitation volume. The diffraction-limited volume within a cell may contain many hundreds to thousands of labeled donor and acceptor biomolecules. Thus, an apparent high FRET signal may be due to ensemble averaging of (1) associations between many donor/acceptors at relatively large separation distances, or (2) associations between a relative few donor/acceptors at small separation distances. Needless to say, either scenario invites a dramatically different interpretation of the underlying biological behavior. However, by implementing HSTED, the uncertainty in how FRET imaging experiments are interpreted is improved. Because the volume represented by each pixel in the image is greatly reduced, the effects of ensemble averaging within that pixel are correspondingly avoided.

Furthermore, FRET can often occur despite the intention of the researcher when imaging multiple biomolecules in a cell. Any spectral overlap between one molecule's absorption profile with another's emission profile will produce some level of energy transfer, thereby confounding any attempts to accurately measure fluorophore abundance. However, the improved spatial resolution of STED combined with hyperspectral detection can also reduce uncertainty is this case, for reasons described above.

The HSTED FRET method described herein includes (1) labeling a sample with at least one FRET pair, the at least one FRET pair comprising a donor fluorophore labeling a first structure and an acceptor fluorophore labeling a second structure, (2) illuminating at least a first optical section of the sample with an illuminating light source to fluorescently excite donor fluorophores in the optical section and, substantially simultaneously, depleting emission from substantially all but a selected subset of the donor fluorophores in the optical section, and (3) collecting polychromatic fluorescence emission data from a multitude of optical sections of the sample. The polychromatic fluorescence emission data may include one or more of (i) fluorescent emission from undepleted donor fluorophores that are not in proximity to an acceptor fluorophore, (ii) fluorescent emission from acceptor fluorophores that are in proximity to undepleted donor fluorophores, or (iii) both.

The method further includes (4) processing the polychromatic fluorescence emission data to identify and localize the fluorescent emission from each of the donor fluorophores and the acceptor fluorophores, and (5) assembling the fluorescence emission data from the multitude of optical sections to produce a three-dimensional, high-resolution map of the proximity of the first structure to the second structure.

Suitable examples of samples that can be labeled with at least one FRET pair include, but are not limited to, purified biomolecules (e.g., proteins and nucleic acids) on a substrate, biomolecules interacting with other biomolecules in solution, prokaryotic cells (e.g., bacteria), eukaryotic cells (e.g., individual human cells or human tissues), a fixed and sectioned tissue, a fixed and sectioned cell, a bacterium, or a virus. Because multiple structures in a cell can be labeled and imaged simultaneously and because the illumination is not destructive, in many embodiments the tissue may be a living tissue. Imaging of living tissue may be particularly attractive because biological processes and the proximity of structures to one another. can be viewed dynamically instead of observing structures in a fixed tissue.

Suitable FRET pairs of dyes are well-known in the art. Examples of Suitable FRET pairs include, but are not limited to, Alexa488/555/590, and the corresponding Atto equivalents, and a Cy5-Cy7 pair.

The present disclosure may be embodied in other specific forms without departing from its spirit or essential characteristics. The described embodiments are to be considered in all respects only as illustrative and not restrictive. The scope of the description is, therefore, indicated by the appended claims rather than by the foregoing description. All changes which come within the meaning and range of equivalency of the claims are to be embraced within their scope.

What is claimed is:

1. A method for multi-color, subdiffraction imaging of a three-dimensional space, comprising:
   providing a sample that includes a three-dimensional space having one or more features of interest that are smaller than an optical diffraction limit;
   labeling the three-dimensional space with two or more different fluorophores having spectrally overlapped excitation and emission wavelengths;
   positioning the sample in a hyperspectral stimulated emission depletion ("HSTED") microscope system that is configured to generate an excitation light beam and a depletion light beam that is substantially coincident with the excitation light beam;
   illuminating an optical section of the three-dimensional space with the excitation light beam and the depletion light beam to excite fluorescence emission from the two or more different fluorophores in the optical section and, substantially simultaneously, depleting emission from substantially all but a selected subset of the two or more different fluorophores in the optical section;
   collecting polychromatic fluorescence emission data from the spectrally distinct emission of each of the two or more different fluorophores, wherein the collecting step further includes,
      collecting fluorescence emission data from a multitude of optical sections of the three-dimensional space, and
      assembling the fluorescence emission data from the multitude of optical sections to produce a three-dimensional, high-resolution image of the three dimensional space; and
   processing the polychromatic fluorescence emission data to identify and localize the fluorescent emission from each of the two or more different fluorophores.

2. The method of claim 1, wherein the depletion light source is configured to generate a torus-shaped depletion zone for depleting fluorescence from the two or more different fluorophores in substantially all but a center portion of the torus-shaped depletion zone.

3. The method of claim 1, wherein the illuminating step comprises transmitting incident light from a supercontinuum light source having an emission range of about 400-800 nm.

4. The method of claim 3, wherein the illuminating step further comprises selecting a wavelength or a range of wavelengths from the supercontinuum light source to excite fluorescence and depletion from the two or more different fluorophores.

5. The method of claim 1, wherein the excitation and depletion wavelengths of the two or more different fluorophores are within a range of about 20-50 nm.

6. The method of claim 1, wherein substantially simultaneously collecting fluorescence emission data from the spectrally distinct two or more different fluorophores includes incorporation of a spectrometer into a detection path.

7. The method of claim 6, wherein the spectrometer permits collection of a complete emission spectrum for all of the fluorophores present in each optical section of the three-dimensional space.

8. The method of claim 1, wherein the three-dimensional space includes a first structure labeled with a first fluorophore and a second structure labeled with a second different fluorophore, and wherein the first structure and the second structure are separated by a distance that is less than the optical diffraction limit.

9. The method of claim 8, further comprising substantially simultaneous collection fluorescence emission data from the first fluorophore on the first structure and second fluorophore on the second structure.

10. The method of claim 8, further comprising resolving the first fluorophore on the first structure from the second fluorophore on the second structure.

11. A method for multi-color subdiffraction imaging of a biological sample, comprising:
    labeling a tissue with two or more different fluorophores having spectrally overlapped excitation and emission wavelengths;
    illuminating an optical section of the tissue with an illuminating light source to excite fluorescence emission from the two or more different fluorophores in the optical section and, substantially simultaneously, depleting emission from substantially all but a selected subset of the two or more different fluorophores in the optical section;
    collecting polychromatic fluorescence emission data from each of the spectrally distinct two or more different fluorophores in the optical section;
    processing the polychromatic fluorescence emission data to identify and localize the fluorescent emission from each of the two or more different fluorophores;
    repeating the illuminating, the collecting, and the processing steps for a multitude of optical sections of the tissue sample; and
    assembling polychromatic fluorescence emission data from the multitude of optical sections to produce a three-dimensional, high-resolution image of the tissue sample.

12. The method of claim 11, wherein the tissue includes one or more features of interest that are smaller than an optical diffraction limit and/or separated by a distance that is less than the optical diffraction limit.

13. The method of claim 11, further comprising labeling a first structure with a first fluorophore and labeling a second structure with a second different fluorophore, wherein the first structure and the second structure are separated by a distance that is less than an optical diffraction limit.

14. The method of claim 13, further comprising substantially simultaneously collecting fluorescence emission data from the first fluorophore on the first structure and second fluorophore on the second structure.

15. The method of claim 14, further comprising resolving the fluorophore on the first structure from the second fluorophore on the second structure.

16. The method of claim 11, wherein the tissue is one or more of a prokaryotic cell, a eukaryotic cell, a fixed and sectioned tissue, a fixed and sectioned cell, a bacterium, or a virus.

17. The method of claim 11, wherein the tissue is a living tissue.

18. The method of claim 11, wherein the two or more different fluorophores have excitation and depletion wavelengths within a range of about 20-50 nm.

19. The method of claim 11, wherein the two or more different fluorophores are at least one of an organic dye or a fluorescent protein.

20. The method of claim 11, wherein the tissue is labeled with two to ten different fluorophores.

21. The method of claim 11, wherein multivariate curve resolution algorithms are used to mathematically isolate underlying pure component spectra from spectrally-resolved STED experiments.

22. The method of claim 21, where a weighted classical least squares algorithm is used in combination with pure component spectra identified from multivariate curve resolution to quantify the relative abundances and localization of the underlying pure components from a spectrally-resolved STED image of a biological sample.

* * * * *